United States Patent [19]

Pettit

[11] Patent Number: 5,561,122

[45] Date of Patent: Oct. 1, 1996

[54] COMBRETASTATIN A-4 PRODRUG

[75] Inventor: George R. Pettit, Paradise Valley, Ariz.

[73] Assignee: Arizona Board of Regents acting on behalf of Arizona State University, Tempe, Ariz.

[21] Appl. No.: 363,406

[22] Filed: Dec. 22, 1994

[51] Int. Cl.$^6$ .............................. A61K 31/66; C07F 9/09
[52] U.S. Cl. ................................ 514/130; 558/210
[58] Field of Search ......................... 558/210; 514/130

[56] References Cited

U.S. PATENT DOCUMENTS 4,996,237  2/1991  Pettit et al. ........................ 514/720

FOREIGN PATENT DOCUMENTS 9216486  10/1992  WIPO .

*Primary Examiner*—Johann Richter
*Assistant Examiner*—Laura Stockton
*Attorney, Agent, or Firm*—Richard R. Mybeck

[57] ABSTRACT

Disclosed herein are Combretastatin A-4 Prodrugs, having the general structure set forth below, which are useful in the treatment of one or more neoplastic diseases by means of chemotherapy.

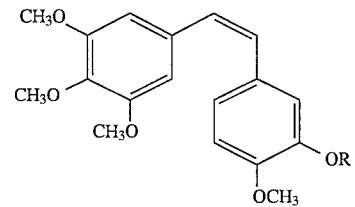

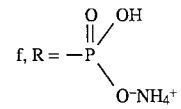

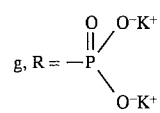

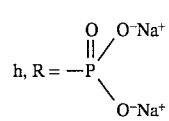

3 Claims, No Drawings

COMBRETASTATIN A-4 PRODRUG

This research was funded in part by Outstanding Investigator Grant CA44344-01-06 awarded by the National Cancer Institute, DHHS. The United States government may have certain rights to this invention.

INTRODUCTION

The present invention relates generally to the field of compounds which may be useful in the treatment of one or more neoplastic diseases by means of chemotherapy. More particularly, this invention relates to the synthesis of a water soluble prodrug of the known antineoplastic compound previously denominated as Combretastatin A-4.

BACKGROUND OF THE INVENTION

The isolation of combretastatin A-4 was disclosed in U.S. Pat. No. 4,996,237 to George R. Pettit et al. issued Feb. 26, 1991. The general background therefrom relating to combretastatin A-4 is incorporated herein, by this reference thereto, as if fully set forth.

The potent cancer cell growth (Von Hoff et al., 1993 and tubulin assembly (Hamel et al., 1989) inhibitor combretastatin A- 4 (1) (Pettit et al., 1989) isolated from the African tree *Combretum caffrum* (Combretaceae) has been undergoing preclinical development. Due to the very sparing aqueous solubility behavior of phenol 1a and its alkali metal salts (cf, 1b, c) drug formulation attempts gave unsatisfactory results. This invention relates to the synthesis of a practical water soluble pro-drug.

BRIEF SUMMARY OF THE INVENTION

Combretastatin A-4 is essentially insoluble in water. This characteristic has significantly interfered with accomplishing the necessary formulations of pharmaceutical preparations of this compound for use in pre-clinical development. Hence, derivatives of the combretastatin A-4 (1a), 3' phenol group were prepared for evaluation as possible water soluble prodrugs. As observed for combretastatin A-4, the sodium salt (1b), potassium salt (1c) and hemisuccinic acid ester (1d) derivatives of phenol 1a were essentially insoluble in water. Indeed these substances regenerated combretastatin A-4 upon reaction with water. A series of other simple derivatives proved unsatisfactory in terms of water solubility or stability or both. The most soluble derivatives evaluated included the ammonium (1f) potassium (1g) and sodium (1h) phosphate salts where the latter two proved most stable and suitable. Both the potassium (1g) and sodium (1h) phosphate derivatives of combretastatin A-4 were also found to exhibit the requisite biological properties necessary for a useful prodrug.

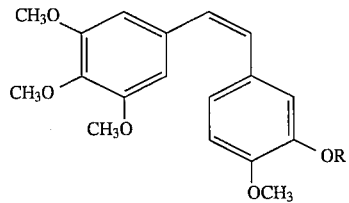

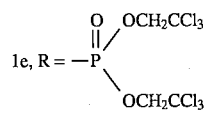

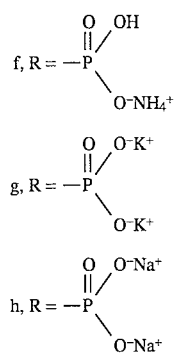

Compound 1h and combretastatin A-4 demonstrate reasonably similar in vitro activity levels in the NCI 60 cell line panel both when the activity level is evaluated and when the COMPARE algorithm is applied thereto.

Accordingly, the prime object of the subject invention is to prepare prodrugs of combretastatin A-4 which are both water soluble and stable, and the means of synthesizing such compounds.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

DESCRIPTION OF THE PREFERRED EMBODIMENT

The process by which combretastatin may be synthesized is well known in the art. See Pettit, G. R. et al., "Isolation and structure of the strong cell growth and tubulin inhibitor combretastatin A-4." Experimentia 209 (1989) and U.S. Pat. No. 4,996,237 issued to George R. Pettit et al. Feb. 26, 1991. Combretastatin A-4 synthesized by that method disclosed in U.S. Pat. No. 4,996,237 ("the 237 patent") was used throughout this process.

3-O-Bis(2,2,2-trichloroethyl)phosphorylcombretastatin A-4 (1e) was synthesized as follows: A solution of bis(2,2,2-trichloroethyl) phosphorochloridate (11.98 g, 32 mmol) in dry pyridine (15 ml) was added to a solution of combretastatin A-4 (5g, 16 mmol) in dry pyridine (60 ml). The mixture was stirred at 25° C. for 15 hours. Analysis by TLC indicated the presence of some unreacted combretastatin A-4. The mixture was heated at 90° C. for 2.5 hours to complete the reaction. The cold reaction mixture was concentrated in vacuo and the residue partitioned between water (100 ml) and methylene chloride (100 ml). The organic phase was washed successively with 1N hydrochloric acid (2×50 ml), water (2×50 ml), saturated sodium hydrogen carbonate solution (2×50 ml), brine (50 ml) and concentrated to a yellow oil which gave a white solid (9.7 g) on trituration with hexane (100 ml). Recrystallization from cyclohexane (14 ml/g) gave 3-O-bis (2,2,2-trichloroethyl) phosphorylcombretastatin A-4 (8.51 g, 82%) as fine colorless prisms: m.p. 88°–89° C.; TLC, $R_f$=0.4 (2:1 hexane-ethyl acetate); UV $\lambda_{max}$ ($CH_3OH$) 219 nm (log $\epsilon$, 4.35), 237 nm (log $\epsilon$, 4.27), 288 nm (log $\epsilon$, 4.12); IR $\nu_{max}$ (KBr) 3007w, 2939w, 2843w, 1570m, 1508m, 1288s, 1101s, 1001s, 900s, 813s $cm^{-1}$; $^1$H-NMR, $\delta$H (300 MHz, $CDCl_3$) 3.67 (6H, s), 3.81 (3H, s), 3.83 (3H, s), 4.67 (4H, m), 6.39 (1H, d J 12 Hz), 6.44 (2H, s), 6.45 (1H, d, J 12 Hz), 6.81 (1H, d, J 9 Hz), 7.09 (1H, dd, J 1.5, 9 Hz), 7.23 (1H, d, J 1.5 Hz); $^{13}$C-NMR, δC (75 MHz, CDCl$_3$) 153.70, 139.32, 139.21, 137.96, 132.84, 130.95, 130.67, 128.68, 128.01, 122.91, 112.82, 106.40, 77.83, 77.77, 61.26, 56.34, 56.28; EIMS m/z 659 (10%, M$^+$) 658 (46%, M$^+$-H) 643 (18%, M$^+$-CH$_4$), 623 (2%, M$^+$-HCl); HREIMS m/z 655.9274 (M$^+$), calc. 655.9262 for C$_{22}$H$_{23}$Cl$_6$PO$_8$.

Anal. calcd for C$_{22}$H$_{23}$Cl$_6$PO$_8$: C, 40.10; H, 3.52; P, 4.70%. Found: C, 40.6; H, 3.64: P, 4.56.

Ammonium hydrogen combretastatin A-4 3-O Phosphate (1f).

Zinc dust (4 g, 61 mmol) was added to a solution of 3-O-bis-(2,2,2-trichloroethyl)phosphoryl combretastatin A-4 (1e) (4.35 g, 6.6 mmol) in pyridine (64 ml) and glacial acetic acid (16 ml). The mixture was stirred at 50° C. under nitrogen for 18 hours. The cooled solution was filtered through a bed (2.5×6 cm) of CELITE. The CELITE was washed with methanol and the washings were combined with the filtrate. The resulting solution was concentrated in vacuo to a brown oil (4.5 g) which was passed through a column of DOWEX 50 (H$^+$ form, 4×100 cm) eluting with 1:1 methanol-water. Removal of the solvents from the UV active fractions gave the phosphoric acid as a brown oil (3.02 g). Conversion to the ammonium salt was accomplished by addition of the oil to a column of DOWEX 50 (NH$_4^+$ form, 4×100 cm) and elution with 1:1 methanol-water. Evaporation of solvents from the UV active fractions led to ammonium hydrogen combretastatin A-4 3-O phosphate (2.04 g, 75%) as a colorless solid: m.p. 177°– 188° C. (decomp); TLC R$_f$=0.66 (4:3:2:1 1-butanol-methanol-water-ammonia; UV λ$_{max}$ (CH$_3$OH) 206 nm (log ε, 4.087), 217 nm (log ε, 4.084), 291 nm (log ε, 3.982); IR ν$_{max}$ (KBr) 3293m, 3277m, 2999m, 2941m, 2843m, 2326w, 1582s, 1514s, 1431s, 1269s, 1240s, 1126s, 1038s, 962s cm$^{-1}$; $^1$H-NMR δH (400 MHz, 1:4 D$_2$O/CD$_3$OD) 3.58 (6H, s), 3.68 (3H, s), 3.75 (3H, s), 6.38 (1H, d, J 12 Hz), 6.53 (2H, s), 6.56 (1H, d, J 12 Hz), 6.71 (1H, d, J 9 Hz), 6.79 (1H, dd, J 1.5, 9 Hz), 7.30 (1H, d, J 1.5 Hz); $^{13}$C-NMR, δC (100 MHz, 1:4 D$_2$O/CD$_3$OD) 153.98, 137.96, 135.54, 134.64, 131.86, 130.84, 129.91, 127.83, 124.49, 123.03, 113.33, 107.43, 61.24, 56.62, 56.46; EIMS m/z 316 (100%, M$^+$ -PO$_3$NH$_4$), 301 (316 —CH$_3$); FAB m/z 414 (8%, [M+H]$^+$), 396 (60%, [M-NH$_3$]$^+$); and HRFAB m/z 396.0969 [M-NH$_3^+$], calc 396.0974 for C$_{18}$H$_{24}$NO$_8$P-NH$_3$.

Dipotassium combretastatin A-4 3-O-phosphate (1g)

Ammonium hydrogen combretastatin A-4 3-O-phosphate (0.10 g, 0.245 mmol) was dissolved in 1:1 methanol-water (2 ml). The addition of 1 drop of concentrated aqueous ammonia was necessary to obtain complete solution. The solution was passed through a column (1×20 cm) of DOWEX 50 (K$^+$ form) eluting with 1:1 methanol-water. Removal of solvent from the UV active fractions gave the dipotassium salt as a cream colored solid (0.11 g, 98%): m.p. 197°–200° C. (decomp); TLC R$_f$=0.67 (4:3:2:1 1-butanol-methanol-water-ammonia; EIMS m/z 316 (100%, M$^+$ —PO$_3$K$_2$ +H), 301 (82%, 316-CH$_3$); HRFAB m/z 473.01675 ([M+H]$^+$), calc. 473.0170 for C$_{18}$H$_{20}$K$_2$O$_8$P.

Disodium combretastatin A-4 3-O-Phosphate (1h).

Ammonium hydrogen combretastatin A-4 3-O-phosphate (0.10 g, 0.245 mmol) was dissolved in 1:1 methanol-water (2 ml) with the aid of 1 drop of concentrated aqueous ammonia. The solution was passed through a column (1×20 cm) of DOWEX 50 (Na$^+$ form). Elution with 1:1 methanol-water and removal of the solvent from the UV active fractions gave the disodium salt as a cream colored solid (0.10 g, 99% yield): m.p. 190°–195° C. (decrap); TLC R$_f$=0.65 (4:3:2:1 1-butanol-methanol-water-ammonia; UV λ$_{max}$ (CH$_3$OH) 218 nm (log ε, 4.16), 292 nm (log ε, 3.78); IR ν$_{max}$ (KBr) 3421m, 2999w, 2939w, 2837w, 1580m, 1510s, 1456m, 1267m, 1236m, 1126s, 995s cm$^{-1}$; $^1$H-NMR δH (300 MHz, D$_2$O) 3.59 (6H, s), 3.69 (3H, s), 3.78 (3H, s), 6.40 (1H, d, J 12 Hz), 6.51 (2H, s), 6.53 (1H, d, J 12 Hz), 6.83 (1H, d, J 9 Hz), 6.91 (1H, dd, J 1.5, 9 Hz), 7.18 (1H, d, J 1.5 Hz); $^{13}$C-NMR δC (75 MHz, D$_2$O) 159.24, 142.86, 142.45, 140.57, 137.22, 136.65, 136.11, 132.15, 128.73, 128.69, 119.81, 113.44, 67.74, 62.78, 62.61; EIMS m/z 316 (100%, M$^+$ -PO$_3$Na$_2$ +H); HRFAB m/z 441.06843 (M+H$^+$), calc 441.06912 for C$_{18}$H$_{20}$ Na$_2$O$_8$P.

Biological Evaluation and Statistical Definitions

The following measures are used to express drug activity by giving the drug dose which reduces cell growth to a specified percentage of growth:

ED$_{50}$ (P388) and GI$_{50}$ (HTCL) are the drug doses needed to reduce the percent growth to 50%. There is no mathematical difference between ED$_{50}$ and GI$_{50}$, which are both calculated using the same formula. The only difference is historical usage.

Total Growth Inhibition ("TGI") is the drug dose needed to yield zero percent growth, i.e., just as many cells at the end of the experiment as were present in the beginning. Whether just as many cells were killed as were produced (steady state), or no growth occurred (total inhibition), cannot be distinguished.

Lethal Concentration 50% ("LC$_{50}$") is the drug concentration which reduces growth to −50%, i.e., removes half of the cells originally present at the beginning of the experiment.

Each drug is tested at five (5) doses: 100 - 10 - 1 - 0.1 - 0.01 µg/ml. Percent Growths are calculated for each dose. The two (or three) doses with growth values above, below, (or near to) 50% growth are used to calculate the ED$_{50}$/GI$_{50}$ using a linear regression formula. The log of the dose is used during the regression computation. If no dose yields a growth value under 50%, the results are expressed as: ED$_{50}$>(highest dose). If no dose yields growth higher than 50% growth, then ED$_{50}$<(lowest dose). Similar calculations are performed for the TGI at 0% growth, and at −50% growth for the LC$_{50}$.

PERCENT OF GROWTH

At the start of an experiment, cells from the in vitro cell cultures are inoculated into the appropriate tubes or microtiter plates. One set of control tubes/plates is immediately counted to determine the number of cells at the start of the experiment. This is the "baseline count" or "T$_{zero}$ reading". At the end of the experiment (48 hours later) a second set of control tubes/plates is analyzed to determine the "Control Growth" value. The growth (or death) of cells relative to the initial quantity of cells is used to define the "Percent of Growth".

|  | EXAMPLE:<br>Baseline Count = 20<br>Control Count = 200<br>(10-Fold Growth) |
|---|---|
| 100% Growth = Control Growth | 100% Growth = 200 |
| 50% Growth = T$_{zero}$ + $\dfrac{\text{Control} - T_{zero}}{2}$ | 50% Growth = 200 |

-continued

| | EXAMPLE:<br>Baseline Count = 20<br>Control Count = 200<br>(10-Fold Growth) |
|---|---|
| 0% Growth = $T_{zero}$ | 0% Growth = 20 |
| −50% Growth = $T_{zero}/2$ | −50% Growth = 10 |

For further information about the testing protocols and procedures see Anne Monks et al., "Feasibility of a High-Flux Anticancer Drug Screen Using a Diverse Panel of Cultured Human Tumor Cell Lines", 83 *J. Nat. Cancer Inst.* No. 11, pp. 757–66 (5 Jun. 1991) and Michael J. Boyd, "Status of the NCI Preclinical Antitumor Drug Discovery Screen" 3 *Princ & Practice of Oncology Updates* No. 10, pp. 1–12 (October 1989).

By definition a pro-drug is a precursor which will undergo metabolic activation in vivo to the active drug. Thus, certain phosphate derivatives make ideal pro-drugs if the phosphate group can be cleaved by endogenous non-specific phosphatases (McComb et al., Alkaline Phosphatase. New York: Plenum Press, 1979) A preliminary in vitro comparison of the stable combretastatin A-4 phosphate alkali metal salts (1g) and (1b) against the P388 murine leukemia and a selection of six human tumor cell lines (OVCAR-3, SF-295, A498, NCI-H460, KM20L2, SK-MEL-5) was performed using the sulforhodamine B assay (Skehan et al., "New Colorimetric Cytotoxicity Assay for Anticancer-Drug Screening" *J. Nat. Cancer Inst.* 1107 (1990)). The disodium phosphate derivative (1h) averaged about 2 to 10-fold more potent than the dipotassium salt (1g) (data not shown). Combretastatin A-4 (1a) and prodrug (1h) were then comparatively evaluated against the full-panel NCI screen (M. R. Boyd, "Status of the NCI Preclinical Antitumor Drug Discovery Screen: Implications for Selection of New Agents for Clinical trial," 3 *Cancer: Principles and Practice of Oncology Updates* No. 10, pp1–12 (1989) and M. R. Boyd et al. "The Future of New Drug Development. Section I. Introduction to Cancer Therapy," *Current Therapy in Oncology*. Philadelphia: Decker (1993)). Both were tested in quadruplicate at each of three different concentration ranges ($10^5$, 10–6 and $10^{-7}$M upper limits, five, $\log_{10}$-spaced concentrations in each range). Optimal tests were selected for overall potency and differential cytotoxicity comparisons (M. R. Boyd and K. P. Paul, "Some Practical Considerations and Applications of the NCI in vitro Anticancer Drug Discovery Screen", *Drug Development Research* (In Press)). The mean panel GIs0 concentration for the parent compound (1a) was $6.61\pm0.79\times10^{-9}$M, compared to $6.89\pm0.96\times10^{-9}$M for prodrug (1h). TGI-COMPARE analyses (Id.) revealed a very high Pearson correlation coefficient of 0.91 for the differential cytotoxicity profiles of combretastatin A-4 (1a) and its prodrug (1h). This high correlation coefficient reflects similarities in biological properties and/or chemical structure and properties. K. D. Paull et al., "Display and analysis of Patterns of Differential Activity of Drugs Against Human Tumor Cell Lines: Development of Mean Graph and COMPARE Algorithm," 81 *J. Nat. Cancer Inst.* No. 14 pp. 108–92 (Jul. 19, 1989).

Clearly, the excellent water solubility of sodium phosphate (1b), good stability and cell growth inhibitory activity comparable to combretastatin (1a) allow selection of this prodrug candidate for drug formulation studies. In a like manner, it is believed that any of the combretastatin A-4 phosphate alkali metal salts can be synthesized and utilized as prodrugs with cell growth inhibitory activity comparable to combretastatin (1a).

Based upon the foregoing compositions 1g and 1h are believed useful in the treatment of one or more neoplastic diseases. For example, acute myelocytic leukemia, acute lymphocytic leukemia, malignant melanoma, adenocarcinoma of lung, neuroblastoma, small cell carcinoma of the lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either of the combretastatin A-4 phosphate alkali metal salts (1b) and (1g).

COMPOSITION "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

COMPOSITION "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 200 mg of an active ingredient, are prepared from the following types and amounts of ingredients:

| | |
|---|---|
| Active ingredient, micronized | 200 g |
| Lactose | 300 g |
| Corn starch | 50 g |

-continued

| | |
|---|---|
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the g used above.

COMPOSITION "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 20 mg of an active ingredient in each milliliter, is prepared from the following types and amounts of ingredients:

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention which is limited only by the scope of the claims appended hereto.

What is claimed is:

1. A compound having the general structure set forth below:

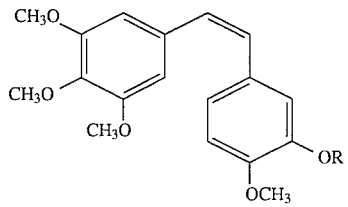

wherein R is

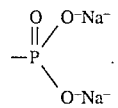

2. A method of treating cells afflicted with a neoplastic disease comprising administering to said cells an effective amount of the active ingredient disodium combretastatin A-4 3-O-phosphate in a pharmacologically acceptable carrier.

3. A method according to claim 2 in which said carrier comprises an aqueous solution.

* * * * *